(12) United States Patent
Hochrainer

(10) Patent No.: US 7,284,553 B2
(45) Date of Patent: Oct. 23, 2007

(54) POWDER INHALER COMPRISING A CHAMBER FOR A CAPSULE FOR TAKING UP A NON-RETURNABLE CAPSULE BEING FILLED WITH AN ACTIVE INGREDIENT

(75) Inventor: Dieter Hochrainer, Schmallenberg (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 40 days.

(21) Appl. No.: 10/728,312

(22) Filed: Dec. 4, 2003

(65) Prior Publication Data
US 2004/0149283 A1 Aug. 5, 2004

Related U.S. Application Data

(60) Provisional application No. 60/438,979, filed on Jan. 9, 2003.

(30) Foreign Application Priority Data
Dec. 12, 2002 (DE) ................................. 102 58 360

(51) Int. Cl.
*A61M 15/06* (2006.01)
(52) U.S. Cl. ................................. 128/203.21
(58) Field of Classification Search ........... 128/200.14, 128/200.22, 203.12, 203.15, 203.21
See application file for complete search history.

(56) References Cited

U.S. PATENT DOCUMENTS

| | | | |
|---|---|---|---|
| 2,569,720 A * | 10/1951 | Jesnig | 128/203.15 |
| 2,604,094 A | 7/1952 | Miller et al. | 128/206 |
| 3,795,244 A * | 3/1974 | Lax et al. | 128/203.15 |
| 3,807,400 A | 4/1974 | Cocozza | |
| 3,918,451 A * | 11/1975 | Steil | 128/203.21 |
| 3,991,761 A * | 11/1976 | Cocozza | 128/203.15 |
| 4,069,819 A * | 1/1978 | Valentini et al. | 128/203.15 |
| 4,116,195 A * | 9/1978 | James | 604/244 |
| 4,210,140 A * | 7/1980 | James et al. | 604/58 |
| 4,884,565 A * | 12/1989 | Cocozza | 128/203.21 |
| 4,889,114 A * | 12/1989 | Kladders | 128/203.15 |
| 5,048,514 A * | 9/1991 | Ramella | 128/203.21 |

(Continued)

FOREIGN PATENT DOCUMENTS

DE 25 29 522 1/1977

(Continued)

*Primary Examiner*—Steven O. Douglas
(74) *Attorney, Agent, or Firm*—Michael P. Morris; Mary-Ellen M. Devlin; Alan R. Stempel

(57) ABSTRACT

The invention relates to a powder inhaler operating on the Bernoulli principle with replaceable cylindrical disposable capsules as the active substance reservoir. The powder inhaler consists essentially of a preferably cylindrical capsule chamber provided with means for laterally opening the capsule, an air inlet opening in the capsule chamber and an air outlet opening and a mouthpiece mounted downstream of the air outlet opening. The capsule chamber is constructed so that after insertion the reservoir capsule can essentially only move in the longitudinal direction when a sufficiently powerful air stream passes through the capsule chamber, guided substantially parallel to the longitudinal axis of the capsule. According to the invention, the inner wall of the capsule chamber is uneven in order to achieve a better emptying of the capsule than is obtained with a smooth inner surface.

2 Claims, 6 Drawing Sheets

| U.S. PATENT DOCUMENTS | | | | |
|---|---|---|---|---|
| 5,372,128 A | * | 12/1994 | Haber et al. | 128/203.21 |
| 5,492,112 A | * | 2/1996 | Mecikalski et al. | 128/203.15 |
| 5,542,411 A | * | 8/1996 | Rex | 128/203.15 |
| 5,647,349 A | * | 7/1997 | Ohki et al. | 128/203.15 |
| 5,685,294 A | * | 11/1997 | Gupte et al. | 128/203.15 |
| 5,947,118 A | * | 9/1999 | Hochrainer et al. | 128/203.15 |
| 5,996,577 A | * | 12/1999 | Ohki et al. | 128/203.15 |
| 6,810,872 B1 | * | 11/2004 | Ohki et al. | 128/203.15 |
| 6,948,492 B2 | * | 9/2005 | Wermeling et al. | 128/200.14 |
| 2002/0134374 A1 | | 9/2002 | Loeffler et al. | 128/200.14 |

| FOREIGN PATENT DOCUMENTS | | |
|---|---|---|
| DE | 3345722 | 6/1985 |
| EP | 0 303 844 | 2/1989 |
| EP | 0911047 | 4/1999 |
| FR | 2146202 | 2/1973 |
| GB | 2 35 6842 | 6/2001 |
| WO | WO 9102558 | 3/1991 |
| WO | WO 0007572 | 2/2000 |
| WO | WO 02/083220 | 10/2002 |

* cited by examiner

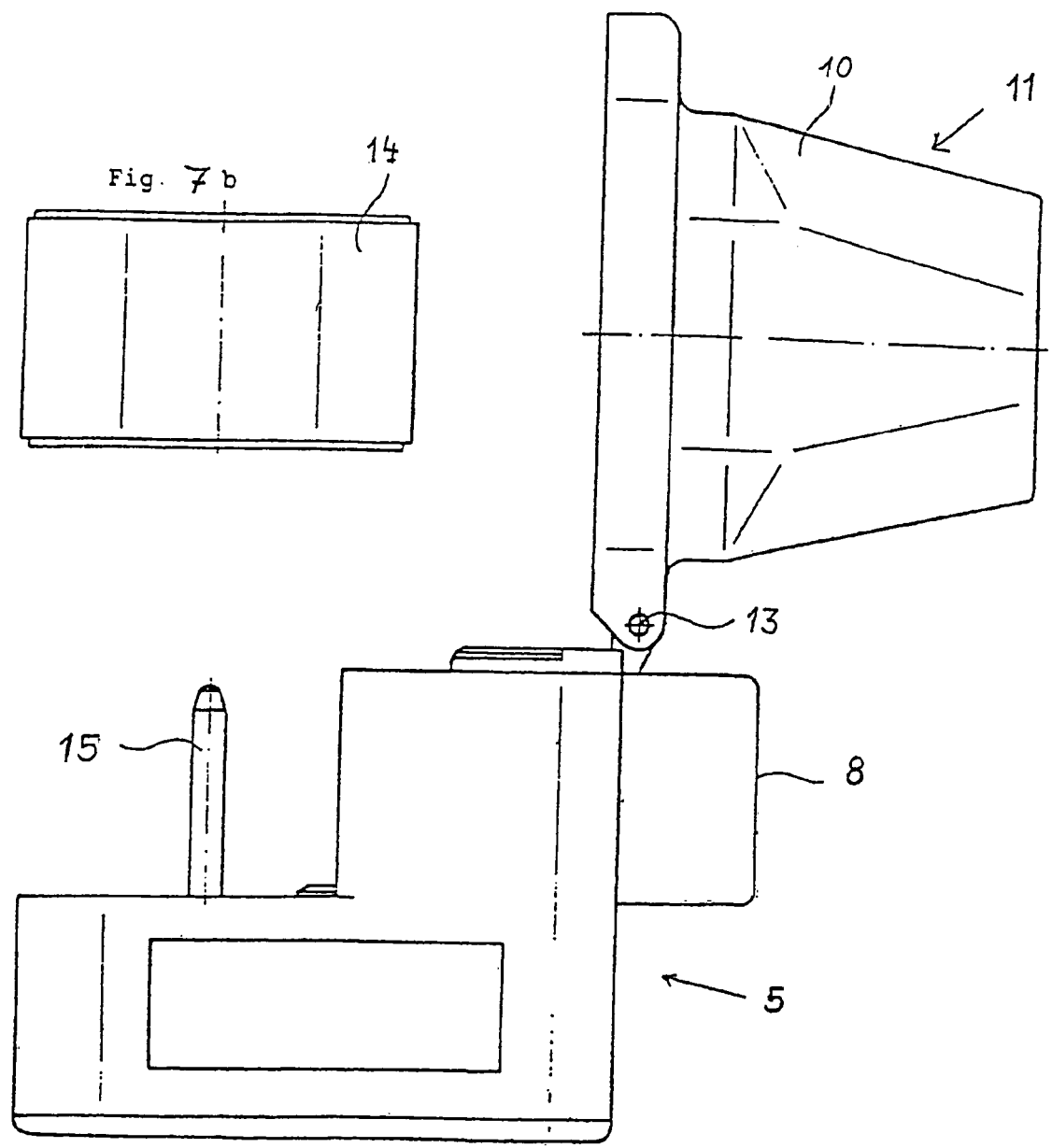

POWDER INHALER COMPRISING A CHAMBER FOR A CAPSULE FOR TAKING UP A NON-RETURNABLE CAPSULE BEING FILLED WITH AN ACTIVE INGREDIENT

RELATED APPLICATIONS

Benefit of U.S. Provisional Application No. 60/438,979, filed on Jan. 9, 2003 is hereby claimed.

FIELD OF THE INVENTION

The invention relates to a powder inhaler operating on the Bernoulli principle with replaceable cylindrical disposable capsules as the active substance reservoir. The powder inhaler consists essentially of a preferably cylindrical capsule chamber provided with means for laterally opening the capsule, an air inlet opening in the capsule chamber and an air outlet opening and a mouthpiece mounted downstream of the air outlet opening. The capsule chamber is constructed so that after insertion the reservoir capsule can essentially only move in the longitudinal direction when an air stream passes through the capsule chamber, guided substantially parallel to the longitudinal axis of the capsule. According to the invention, the inner wall of the capsule chamber is uneven in order to achieve a better emptying of the capsule than is obtained with a smooth inner surface.

PRIOR ART

A number of powder inhalers operating by the Bernoulli principle are known in the literature. What they all have in common is that the active substance to be delivered is stored in a cylindrical capsule and this capsule is inserted in a capsule chamber of the inhaler. The capsule chamber is usually cylindrical in shape, being somewhat longer and wider than the capsule so that the capsule is able to vibrate longitudinally, i.e. in the direction of air flow, and also transversely, i.e. at right angles to the direction of flow, but remains aligned substantially parallel to the chamber axis. The capsule chamber has an air inlet near one of its two ends and an air outlet opening in the region of the other end. The air outlet leads to a mouthpiece. In order to deliver the active capsule contents, first of all the capsule is opened, normally at two places on its longitudinal casing. As a rule these openings are located close to the two longitudinal ends of the capsule. If an air stream is now generated from the air inlet towards the air outlet in the capsule chamber, it runs along the longitudinal axis of the capsule and has two effects: on the one hand the capsule is moved mainly along its longitudinal axis by the air stream. This movement may also occur intermittently so that the capsule vibrates. On the other hand, the air flowing along the two capsule openings produces a lower pressure in front of the capsule openings than inside the capsule, so that the powder contained in the capsule is picked up by the air stream and thereby nebulised.

The capsules normally used for inhalers of this kind consist of two cup-like components which fit telescopically one inside the other. The outer shape of a composite capsule of this kind is that of a closed cylinder with hemispherical ends. The cylinder has a longitudinal axis and a transverse axis. The longitudinal axis is the axis which runs parallel to the generatrix of the cylinder casing. The longitudinal axis is longer than the transverse axis with the result that the longitudinal section of the capsule has an oval geometry and the cross section has a circular geometry.

Usually, the capsules for inhalable powders consist of hard gelatine but may also consist of a plastic material. In connection with this reference is made to EP 1100474.

DE 3345722 discloses an inhaler of this kind as described at the beginning of this section (Prior art) consisting of two housing elements which are radially moveable towards each other, with a single capsule chamber. The inner surface of the hollow cylindrical capsule chamber is smooth.

WO 91/02558 discloses another inhaler as hereinbefore described wherein instead of a single capsule chamber there are a plurality of capsule chambers arranged in a similar manner to a revolver magazine. The open ends of this magazine are delimited by walls, the air inlet or air outlet being located only at one point in these walls. This magazine is mounted to be rotatable so that a capsule chamber is only connected to the air inlet, the air outlet and the cutting elements required to open the capsule in a certain position.

EP 0911047 discloses an inhaler with a) a cup-shaped lower part open upwardly, b) a plate which covers the opening in the lower part and perpendicular to which is formed a capsule chamber of the kind described above, whilst on the capsule chamber is provided a button which is moveable against a spring which has two sharp spikes for opening the capsule, c) an upper part with a mouth tube which is connected to the capsule chamber, and capable of conveying a powder aerosol, and d) a lid. The elements a), b) c) and d) are joined together by a common hinge element so that they can be flipped relative to each other. In addition, this patent application describes a capsule holder wherein the capsule holder may be constructed as a hole in the plate b) and has ribs at the edge. The capsule is jammed into this capsule holder to hold it in readiness.

FR-A-2 146 202 describes an inhaler with a flat cylindrical chamber in which only the capsule can be moved. The capsule opened at the ends rotates during the inhaling process, driven by tangentially incoming air, about its transverse axis.

U.S. Pat. No. 4,069,819 describes an inhaler wherein the capsule is pierced through the base of the capsule chamber and during inhalation is set in motion by the air flowing in tangentially in the region of the base.

DESCRIPTION OF THE INVENTION

Surprisingly, it has now been found that the delivery of the active substance can be improved using the powder inhaler described above which is known from the prior art and more uniform emptying of the capsules can be guaranteed, if the capsule chamber is not only of the optimum size, larger than the capsule, but if it has an inner surface structure in the form of a relief which is capable of guiding the capsule during vibrations in the capsule chamber. Only capsule chambers with a smooth inner surface are known from the prior art.

The measure adopted according to the invention ensures that the capsule containing the active substance can basically only move back and forth in the capsule chamber by a short distance along its longitudinal axis and has only limited play along its transverse axis and is nevertheless uniformly emptied. In addition, the points of contact of the capsule with the inner chamber surface are also minimized and in this way the vibration is simplified.

It is therefore an aim of the present invention to provide powder inhalers having disposable capsules as the active substance reservoir which improve the delivery of the active substance.

A further aim of the invention is to modify powder inhalers of this kind so as to guarantee uniform emptying of different capsules.

A further objective is to provide a powder inhaler of this kind having a capsule chamber in which a reservoir capsule can move freely in the longitudinal direction.

A further objective is to provide a powder inhaler of this kind having a capsule chamber in which a reservoir capsule can move only slightly in the transverse direction, without interfering with the longitudinal movement of the capsule.

A further aim is to provide powder inhalers having capsule chambers wherein the area of contact between the inner surface of the chamber and the capsule surface is minimized.

Another aim is to provide powder inhalers having capsule chambers in which a degree of emptying of more than 60% and preferably more than 90% is regularly achieved.

SPECIFIC DESCRIPTION OF THE INVENTION

For the powder inhalers according to the invention it is possible to use the inhalers described in the prior art section hereinbefore, particularly those described in DE 3345722, WO 91/02558 or EP 0911047. This means that the features mentioned for the powder inhalers generally described in the prior art section also refer to the powder inhaler according to the invention, with the exception of the features mentioned regarding the shape of the inner surface of the capsule chamber, and need not therefore be specifically mentioned at this point. The capsules mentioned in the same section may be used in the inhaler according to the invention.

The outer shape of the capsule chamber is of no significance for the purposes of the present invention. The outer shape is determined by the position of the capsule chamber and any movements thereof in the inhaler or the movements of other parts of the inhaler around the capsule chamber.

The inner shape of the capsule chamber is designed according to the invention so that it comprises a cavity open on two sides for accommodating a disposable capsule for pharmaceutically active inhalable substances. Preferably, these two openings are provided at opposite ends or immediately adjacent these ends. The inner form may for example be a preferably uniform cylinder or cuboid. Preferably the inner configuration resembles a cylinder.

The dimensions of the capsule chamber are matched to those of the capsule. As an illustration some examples of typical capsule dimensions will now be given, indicating the size of the capsule chamber.

Total length of the closed capsule: 26.1±0.3 mm; 23.3±0.3 mm; 24.2±0.3 mm; 21.7±0.3 mm; 19.4±0.3 mm; 18.0±0.3 mm; 15.9±0.3 mm; 14.3±0.3 mm; 11.1±0.3 mm.

Outer diameter of the capsule body: 9.55 mm; 8.18 mm; 7.36 mm; 7.34 mm; 6.63 mm; 6.07 mm; 5.57 mm; 5.05 mm; 4.68 mm.

External diameter of the capsule caps: 9.91 mm; 8.53 mm; 7.66 mm; 7.64 mm; 6.91 mm; 6.35 mm; 5.83 mm; 5.32 mm; 4.91 mm.

The standard commercial capsules are size 3, which is known at least in Germany. In the telescopic capsules described the diameter of the upper part is 5.83 and the diameter of the lower part is 5.57 mm.

The capsule chamber according to the invention has an inner surface structure which defines an inner cavity enclosed thereby. By the inner cavity is meant the geometric space which comes into contact with the inner surface of the capsule chamber without being penetrated by any surface structures provided. Preferably, it is the corresponding cylindrical space with the largest diameter which can be fitted within the surface structures.

The inner cavity preferably has a diameter which is 1.1 to 2.5 times as great as the capsule diameter. Preferably, the diameter is 1.1 to 2.2 times, more particularly 1.2 to 1.6 times as great as the capsule diameter. The length of the inner cavity of the capsule chamber is 1.02 to 2 times the length of the capsule, preferably 1.04 to 1.8, more particularly 1.1 to 1.6 times the length of the capsule. The diameter of the chamber should be less than the length of the capsule, so that the capsule is held in the longitudinal direction in the chamber and cannot tilt to one side.

As already emphasized, the capsule chamber has two openings, an inlet for incoming air and an air outlet. The air inlet is smaller in cross section than the capsule chamber so that in this region of the capsule chamber the flow velocity of the air is relatively high and a powder in the capsule is delivered by the Bernoulli effect. The air inlet opening is conveniently arranged centrally in the base of the chamber.

On the air outlet side there may be a perforated plate or other device such as projecting components to prevent a capsule moving in the capsule chamber from blocking the air outlet or any capsule fragments formed from being sucked into the mouthpiece.

The perforated plate may for example be part of a funnel-shaped connecting member which can be fitted on to the start of the inhalation channel leading to the mouthpiece in such a way that the edge of the funnel with the perforated plate engages in a plate-shaped insert which forms the base of the mouthpiece. The perforated plate may, however, also be replaceably fixed by jamming it between the funnel edge of the connecting member and a stop of the plate-shaped insert.

A plurality of openings may also be provided as the outlet opening. The cross section available for the air to flow out of the capsule chamber is conveniently greater at every point than the air inlet opening so that the air charged with the pharmaceutical composition can flow out unimpeded as far as possible. The air outlet opening is expediently arranged centrally in the top of the chamber but may also be arranged to one side in the top region.

The provision of the two openings is intended to guide an air stream axially through the capsule chamber.

The capsule chamber has at at least one point along its longitudinal axis (in relation to the interior of the capsule chamber) an opening for or a connection to a cutting device which is provided with at least two sharp spikes or cutters for piercing or cutting open a capsule located in the capsule chamber. Preferably there are at least two such places, with a cutter or spike being able to act on the capsule through each of these places. The cutting device is moveable into the interior of the chamber counter to the pressure of the spring and is operated by means of a spring mounted actuating button.

The points or cutting edges of the cutting device are preferably arranged so that they can penetrate into the upper or lower region of the capsule. As the length of the capsule chamber is adapted to the length of the pharmaceutical capsules, the cutters are preferably located close to the top or bottom end of the capsule chamber. The side wall of the capsule chamber may have radial bores or oblong slots in the region of its top and bottom end which face the spikes or cutting edges and serve to allow the spikes or cutters to pass through. The dimensions of these bores/slots are matched to the cross section of the spikes or cutting edges.

In a preferred embodiment the guide for the spikes of the cutting device comprises a sealing plate. In this way the seal between the capsule chamber in the inhaling position and the cutting device is improved. For the spring mounting of the sealing plate it is possible to use the spring which resets the actuating button for the cutting device.

Finally, in another embodiment, a lever system is provided for actuating the cutting device. This lever system is preferably actuated by an actuating button mounted on the base or side of the housing of the inhaler. The lever system may consist of a rocker and a toggle lever, while the actuating button acts on one end of the rocker and the other end of the rocker presses on one end of the toggle lever, the other end of the toggle lever secured to the cutting device pushing the cutting device forward. The rocker and toggle lever are preferably mounted to be pivotable about axes in holders secured to the housing.

The capsule is supposed to be opened close to both its ends for the inhalation process. The hemispherical caps of the capsule should not be damaged in their central region. This is important because the capsule or caps of the capsule act as a sort of valve. Because of the pressure conditions the capsule is pulled towards the inlet opening counter to the inflowing air and closes it off. As the user continues to suck on the mouthpiece, suction is produced in the capsule chamber by which the capsule is carried towards the air outlet with the inflowing air. The suction now formed at the air inlet ensures that the capsule is pulled towards the inlet opening again. The entire process is repeated in rapid succession as long as the patient continues to inhale through the mouthpiece and sets the capsule vibrating strongly in the axial direction.

The capsule chambers for powder inhalers known from the prior art have a contour-free inner surface. According to the invention, the structure of the inner surface of the capsule chamber is different from a smooth surface.

This is achieved by forming spacers from the capsule, in the form of raised elements, on the inner surface of the capsule chamber, which is also referred to simply as the surface of the capsule chamber, for the purposes of the present invention.

The spacers are such that their points which are furthest from the surface align the capsule axially and promote axial movement of the capsule in the chamber. At the same time the spacers should not jam the capsule laterally, but should allow slight lateral movement of the capsule.

The height of the spacers (i.e. the spacing between the base and the apex) is preferably from 0.1 mm to 5 mm, more preferably from 0.5 mm to 2 mm.

The raised elements are preferably at equal spacings from the capsule in the capsule chamber. These spacings are preferably 0.1 to 1 mm, more preferably 0.2 to 0.5 mm.

The raised elements may be in the form of ribs with sharp edges, with soft undulating transitions or in the form of pins. Combinations thereof are also possible.

The tips or edges of these raised elements preferably have a minimal surface area.

In the case of ribs, these may be arranged axially, i.e. parallel to the longitudinal axis of the capsule in the chamber, transversely, i.e. perpendicularly to the longitudinal axis of the capsule or askew with respect to the longitudinal axis of the capsule. The term "askew" also includes helically arranged ribs.

If the ribs are arranged axially, the capsule chamber expediently has at least three or more such ribs. Preferably it has no more than nine, most preferably not more than six ribs of this kind. The length of the ribs is selected so that they guide the capsule as it moves axially without blocking this movement. Preferably, the ribs extend over the full height of the chamber. In this case the ribs preferably have a triangular cross section, one point of the triangle pointing away from the inner surface of the capsule chamber. This embodiment has the advantage that the capsule can be guided in the capsule chamber without any great frictional losses during its axial movement. Other geometric shapes for the ribs are also possible, e.g. ribs with a semicircular or rectangular cross section, etc.

To prevent the capsule from becoming jammed in the axially arranged ribs, these ribs may be arranged so that the arrangement does not appear rotationally symmetrical in cross section. In other words, where there are three ribs, for example, two of the ribs are closer to one another than to the third rib.

If the ribs are arranged tangentially, all the edges pointing towards the capsule should describe the shape of a uniform cylinder. In the case of ribs running around the periphery of the casing of the capsule chamber it is essential that the spacings between the ribs be designed so that the axially moving capsule cannot be impeded in its movement by a rib of this kind. In this case, at least two ribs are preferred. In cross section they preferably have soft transitions, i.e. an undulating surface. This construction has the advantage that the cross section of the capsule chamber along the longitudinal axis varies constantly, so that when air flows axially along the longitudinal axis of the capsule chamber there may be slight pressure differences which promote the emptying of the capsule.

A further embodiment of the capsule chamber comprises an inner surface with an undulating transverse pattern as described above, with ribs formed axially on this surface, i.e. perpendicularly to the undulations. These ribs are in turn designed so that the outer edges of the ribs are equidistant to the central longitudinal axis of the capsule chamber and therefore the outer edges of the ribs do not have an undulating surface but a surface which is not curved (parallel to the longitudinal axis).

In the case of pin-shaped raised elements these may either be arranged in linear manner and optionally replace the ribs or they may be randomly arranged. The pins will in any case be aligned so that the axial movement of the capsule cannot be disrupted but on the contrary the capsule is guided in its movement.

The present invention also relates to an assembly of at least two capsule chambers which are structurally joined together. Such an assembly may be for example a magazine or revolver magazine with 3, 4, 5, 6, 7, 8, 9, 10, 11, 12, 13, 14, 15, 16, 17, 18, 19, 20, 21, 22, 23, 24, 25, 26, 27, 28, 29, 30 or more capsule chambers. These may be arranged in a circle, helix or spiral with one another, the top ends of the capsule chambers all pointing in the same direction. By the top end is meant the end close to which or on which is found the air outlet opening and on which the top of the capsule abuts (the narrow end of the capsule). Preferably, in a revolver magazine of this kind, the capsule chambers are arranged in a circular or spiral pattern.

The capsule chamber according to the invention may be incorporated in suitable powder inhalers. The powder inhalers thus modified by the capsule chamber according to the invention, which in the simplest case consist of the capsule chamber, an air inlet opening, an air outlet opening connected for air flow to a mouthpiece and optionally a device for opening the capsules, are also a subject of the present invention.

The air mixed with the pharmaceutical substance in the chamber is passed through the mouthpiece to the mouth of the user. The mouthpiece, which is generally tubular and optionally somewhat flattened, may be arranged axially or at an angle to the axis of the chamber or offset laterally from the axis of the chamber.

The mouthpiece of the inhaler may be constructed in the form of a cap which is fitted on to the underlying component (lower part) of the inhaler which contains the capsule chamber. This cap may be hinged to the edge of the inhaler housing so as to be pivotable about an axis extending perpendicularly to the longitudinal axis of the inhaler. The mouthpiece and the lower part of the inhaler housing may, however, also be fixed to one another by a conventional push-fit connection. In any case, access generally, to the capsule chamber and to the cutting device in the lower housing part, on the one hand, and to the inner components such as the perforated plate and the upper housing part (of the mouthpiece-cap) is made substantially easier by the removability or pivotability of the two components.

In order to replace used capsules with fresh ones, in an embodiment of this kind the mouthpiece is flipped upwards or the push-fit connection between the mouthpiece and the lower housing part is undone. The capsule chamber is then freely accessible, so that the emptied capsule can be removed and a full one inserted. The device is then flipped shut or pushed shut.

The inhaler according to the invention allows the pharmaceutical composition to be delivered more reliably with a lower standard deviation compared with the devices known from the prior art. Compared with many devices it also has the additional advantage of better breaking up of any clumps. In fact, the micronised pharmaceutical compositions in the capsules have a tendency to form clumps. These clumps are therapeutically undesirable as it is important for the pharmaceutical composition to be distributed as finely as possible. When the inhaler according to the invention is used the clumps are substantially destroyed.

Preferred inhalers are those described hereinbefore as embodiments of DE 3345722, WO 91/02558 or EP 0911047. Reference is hereby made once again to the features mentioned in this section. The inhaler as described hereinbefore in connection with EP 0911047 is particularly preferred.

In inhalers of this kind there can only be one capsule chambers according to the invention, in accordance with the remarks on DE 3345722 or EP 0911047. However, the capsule chamber may also be part of a capsule chamber magazine as described in WO 91/02558.

An inhaler of this kind has a revolver magazine with a plurality of usually tubular chambers each loaded with one capsule. The magazine is covered at each of its two open ends by a plate, one plate containing the air inlet opening and axially thereto the other plate containing the air outlet opening. As the magazine is rotatably mounted within these plates, one of the chambers can be pivoted into place between the two openings and thus form part of the continuous channel for the inhaled air. After an inhalation process has ended the revolver magazine is further rotated until the next chamber enters the air throughflow channel. One of the two plates may be separated from the magazine, for example, in order to remove used capsules from the chambers, or else the entire magazine can be removed for refilling, for example.

According to this feature of the invention the revolver magazine is releasably mounted in the inhaler housing. After the capsules in the revolver magazine have been used the entire revolver magazine can be replaced or refilled with capsules.

The inhaler housing may have an eccentrically mounted pin on to which the revolver magazine can be fitted.

In order to fix the position of the revolver magazine it may be provided with recesses associated with the capsule chambers for a spring-mounted locking bolt arranged in the inhaler housing. The recesses are arranged so that the locking bolt only engages therein when one of the capsule chambers is located precisely between the air inlet and outlet.

In this way it is possible to ensure that the revolver magazine does not move during the inhalation. The spring mounting of the locking bolt should be selected with regard to the spring constant so that accidental rotation of the revolver magazine is prevented by the locking but on the other hand if greater force is applied the revolver magazine can be rotated out of its locked position. Conical shapes for the free end of the locking bolt and suitably shaped recesses have a supporting effect.

The locking bolt is preferably arranged coaxially with the air throughflow channel underneath the capsule chamber and has a through-bore which simultaneously forms the air inlet in the base. Preferably, the locking bolt is centrally mounted in the inhaler housing. According to another embodiment of the invention the locking bolt is acted upon by a spring the other end of which abuts on a stopper releasably fixed in the inhaler housing, which also has a central through-bore which is part of the air throughflow channel.

In a preferred embodiment the recesses for engagement of the locking bolt in the base are arranged in the base plate of the magazine, concentrically with the air inlet bores of the capsule chambers and like the casing constructed in the form of a flat truncated cone with its base facing outwards. Thus, these recesses are conical or funnel-shaped widenings of the air inlet bores, the widened area facing the locking bolt. The slopes produced by the widening correspond approximately to the chamfers on the top of the locking bolt.

In a preferred embodiment these recesses have an encircling stop edge on the base of the casing of the truncated cone, but also in the base plate, which acts as a rotation preventer or stop for the head of the locking bolt when the latter has engaged in the corresponding recess. Because of this stop edge the magazine cannot be turned any further once the locking bolt has engaged.

According to another feature of this embodiment the said stop edge takes up only part or half of the periphery of the conical recess, i.e. the funnel-shaped widening, and is arranged so that when the locking bolt is engaged it prevents rotation of the magazine in one direction but allows it in the other direction, as the sloping wall of the funnel-shaped widening merges smoothly into the exterior of the base plate.

In another preferred embodiment only one of the recesses has a stop edge which takes up the entire circumference of the recess so that when the locking pin is engaged it is impossible for the magazine to rotate in this recess. This position is then regarded as the end position of a magazine in which all the capsules have been used. In this embodiment, all the other recesses only have a rotation preventer on one side, i.e. effective in one direction, so that the magazine can only ever be rotated in the direction in which a capsule chamber containing an unused capsule is brought into play, until the end position described above in which locking is complete is reached. The user then knows that the magazine has to be loaded with fresh capsules once this last capsule has been used.

In another preferred embodiment a tongue may be fixed to the locking bolt which extends as far as a stop on the inside of the operating button of the cutting device when the locking bolt assumes its upper stop position with the revolver magazine removed. In this position the said tongue acts as a barrier for the cutting device. When the magazine is inserted the locking bolt is pressed down again and in this way the barrier for the cutting device is removed.

The actuation of the cutting device may also be coupled to the rotary movement of the capsule magazine, so that at the press of a button first a capsule chamber is brought into the correct position and then the cutting device is engaged.

If the revolver magazine and the part of the inhaler housing adjacent thereto are constructed with n angles, where n is a whole number indicating the number of capsule chambers, the side surfaces of the inhaler housing part and of the revolver magazine may advantageously be aligned when the magazine is in the correct position. It is then possible to determine immediately from outside whether the chamber is located in the air channel defined by the air inlet and the air outlet.

As an alternative to the construction of the inner surface of the capsule chamber according to the invention, the outer surface of the capsule may also have a surface structure of this kind. In other words, the invention also encompasses capsules for inhalation having a surface structure which corresponds in its function to the surface structure of the capsule chamber. Thus, for example, the capsules may have axial ribs, raised elements, annular rings and the like. The surface structure described with regard to the construction of the surface of the inner wall of the capsule chamber is in this case "projected" onto the outer surface of the capsule. Where axial ribs were described for the capsule chamber, for example, with a triangular cross section, with one of the sides arranged on the surface to form the base and the apex facing the capsule, the capsule may instead have axially arranged ribs on its exterior, which face towards the walls of the capsule chamber. The same applies to other embodiments of the surfaces.

In the inhalation systems according to the invention consisting of a capsule and inhaler, preferably only one of the two elements, i.e. the capsule chamber or the capsule, preferably the capsule chamber, has the structured surface.

The invention will now be described in more detail with reference to the Figures.

FIGS. 7a to d show a powder inhaler with a revolver magazine which contains a plurality of capsule chambers according to the invention.

Figure 8:
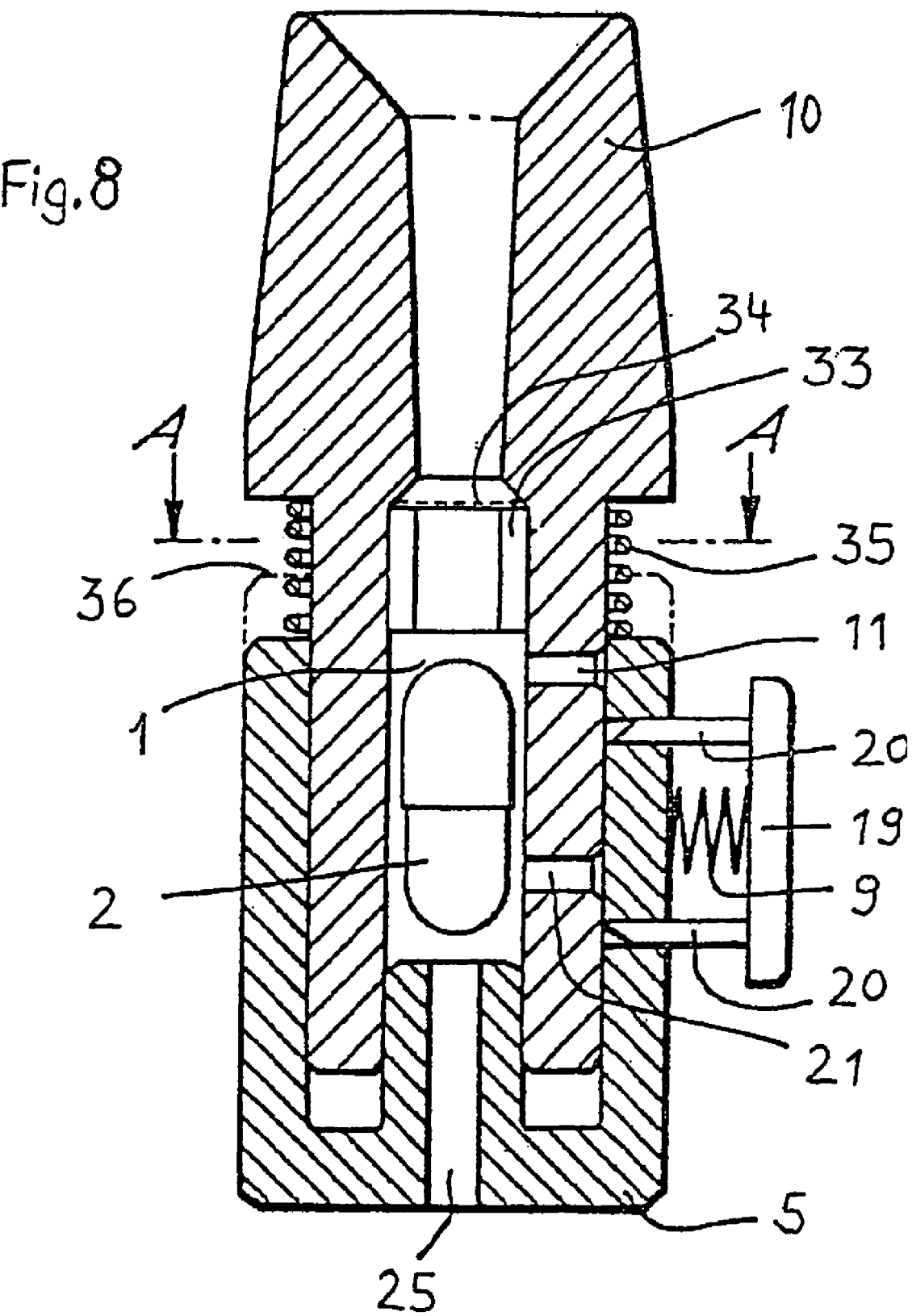

FIG. 8 shows a powder inhaler with an upper part and lower part which are movable relative to each other.

Figure 1:
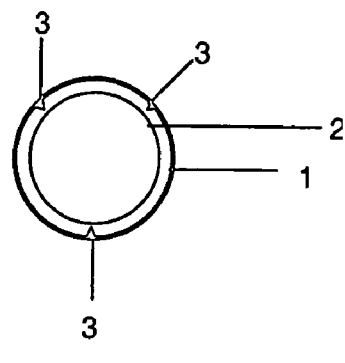
FIG. 1 shows a cross section through a cylindrical capsule chamber according to the invention with 3 longitudinally mounted ribs.

FIG. 1 shows a cross section through a cylindrical capsule chamber (1) according to the invention with 3 longitudinally arranged ribs (3). In the capsule chamber (1) is a disposable capsule for inhalation (2).

Figure 2:
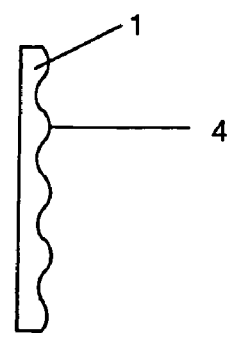
FIG. 2 shows a longitudinal section through the wall of the cylindrical capsule chamber according to the invention with undulating ribs.

FIG. 2 shows a longitudinal section through the wall of the cylindrical capsule chamber (1) according to the invention with undulating ribs (4). Only one side of the wall is shown.

Figure 3:
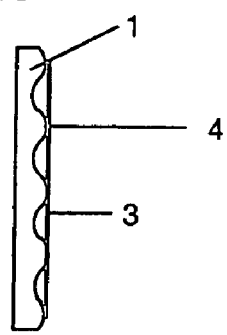
FIG. 3 shows the embodiment according to FIG. 2 in conjunction with the embodiment according to FIG. 1 as a longitudinal section through the wall of the cylindrical capsule chamber according to the invention.

FIG. 3 shows the embodiment according to FIG. 2 in longitudinal section, showing additional ribs (3) in the longitudinal direction according to FIG. 1, which are perpendicular to the undulating ribs (4).

Figure 4:
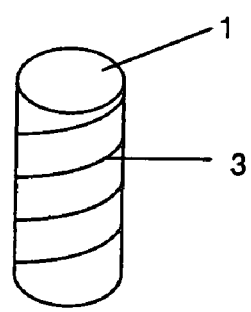
FIG. 4 shows a capsule chamber according to the invention with a helically mounted rib.

FIG. 4 shows a capsule chamber (1) according to the invention with helically arranged ribs (3).

Figure 5:
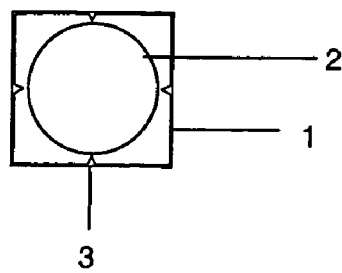
FIG. 5 shows a capsule chamber according to the invention of square cross section.

FIG. 5 shows a capsule chamber (1) according to the invention with a square cross section and 4 longitudinal ribs (3).

Figure 6:
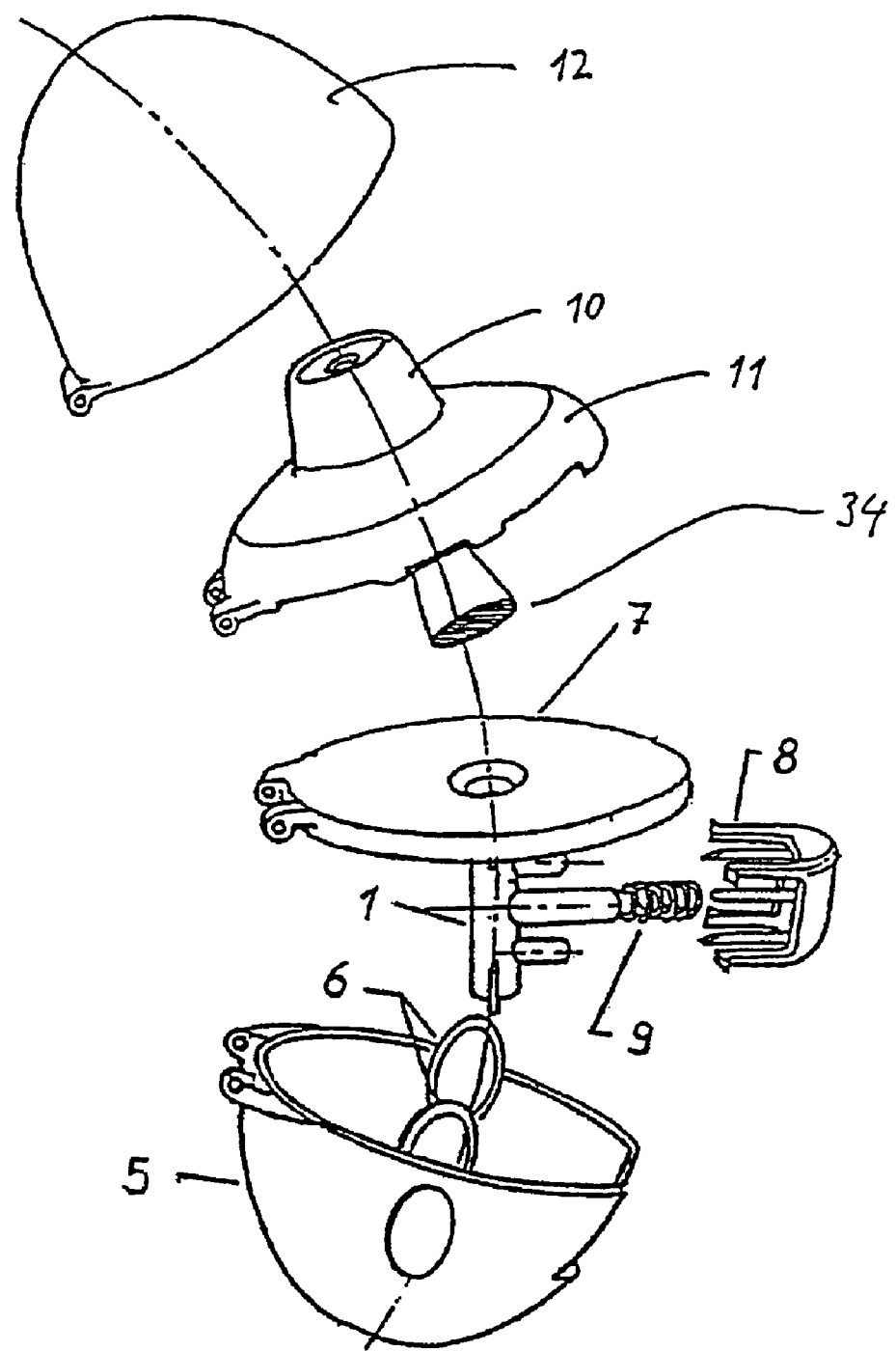
FIG. 6 shows an inhaler with the capsule chamber according to the invention.

FIG. 6 shows how an inhaler may be constructed in which a capsule chamber according to the invention is integrated. Located in a lower part (5) optionally with two windows (6) is a plate (7) connected to the capsule chamber (1). The capsules in the capsule chamber (1) are opened by means of a button (8) provided with two specially sharpened spikes which is pressed in counter to the pressure of the spring (9) and thereby cuts open or pierces the capsule in the chamber in two places. As the user inhales through the device using the mouthpiece (10) which is connected to the upper part (11), the air enters the lower part (5) and from there goes into the capsule chamber (1) according to the invention at the lower end. The device is closed off by a lid (12), which is hinged to the lower part (5), the plate (7) and the upper part (11), so that when the lid is closed dust cannot enter the device. In the plate (7) there may optionally be capsule holders in the form of blind bores. Advantageously, there is a perforated plate (34), which is fixed to the lower end of the mouth tube (10) or of the inhalation channel leading to the opening of the mouthpiece and, when the inhaler is in the closed position, covers the air outlet opening of the capsule chamber (1). The drawings do not show optional snap-fit hooks on the side of the mouth tube (10) or of the upper part (11) which is oriented towards the plate (7), which are capable of engaging in the plate (7). In this case the plate (7) has suitably complementary devices (depressions or holes). Projections or snap fit hooks may also be provided laterally on the plate (7), for example to enable the plate (7) to engage in the lower part. The above mentioned devices for engaging the mouthpiece (10) or upper part (11) in the plate (7) or the plate (7) in the lower part (5) are such that the individual elements can easily be separated from one another again. In addition, a lug may be formed on the point on the lid (12) which is located above the button (8) in the closed position so that this lug engages in a depression on the top of the button (8) and blocks the button (8), so that the button (8) cannot be pressed in the closed position. This prevents the capsule from being accidentally perforated prematurely once it has been inserted in the capsule chamber.

Figure 7C:
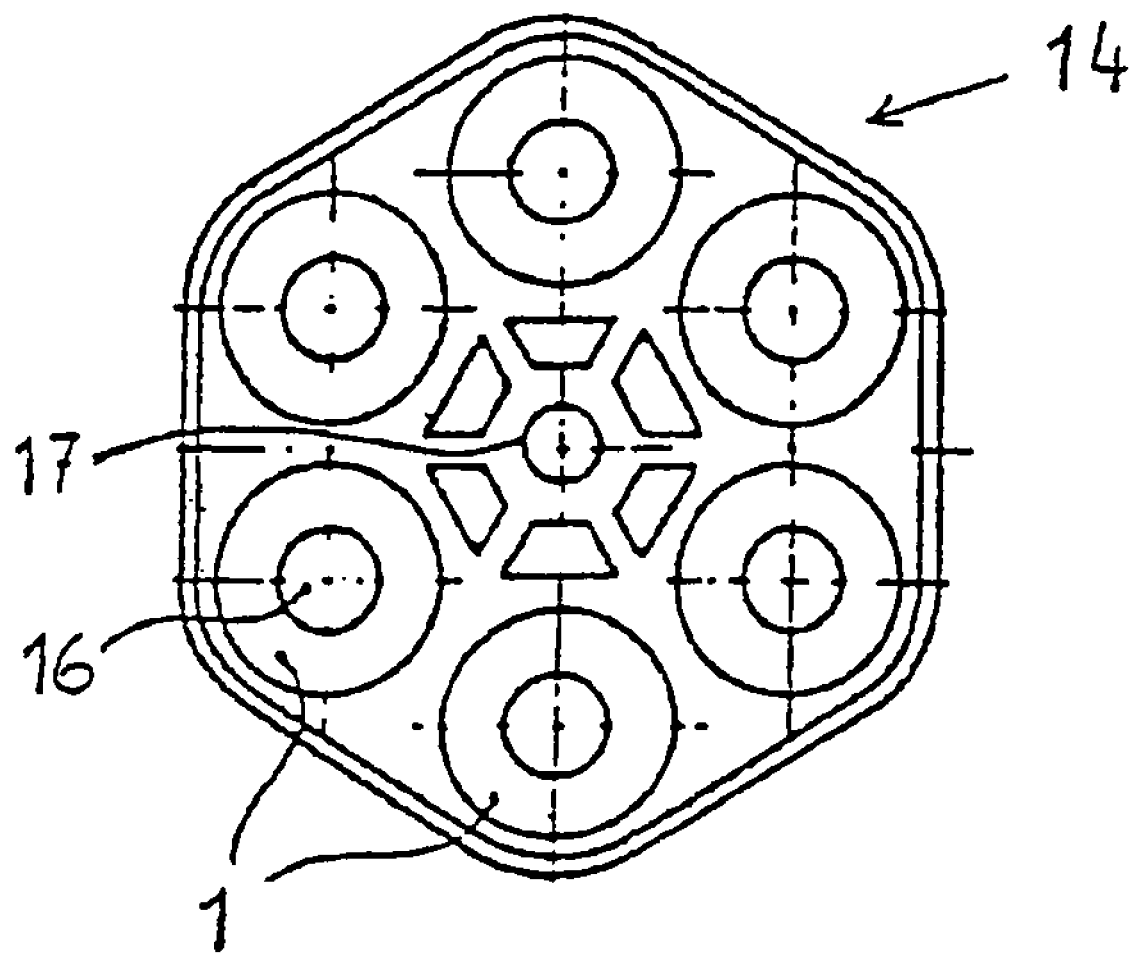

FIG. 7: As can be seen from FIGS. 7a, 7b and 7c, an inhaler with a revolver magazine consists essentially of an inhaler housing (5) with a mouthpiece (10) which is hinged laterally to the upper edge of the inhaler housing (11) so as to be pivotable about an axis (13), and a revolver magazine (14) with the chambers (1) according to the invention for accommodating the capsules. The revolver magazine (14) can be fitted on to a pin (15) eccentrically mounted in the inhaler housing (5). After the revolver magazine (14) has been pushed on the mouthpiece (10) is moved into its normal position—as a cap on the housing; the inhaler is ready for use. A capsule (not shown) can now be perforated by pressing the button (8). As can be seen from FIG. 7c, the revolver magazine (14) in this case has 6 chambers (1) for accommodating the capsules (not shown). The base of each chamber (1) has an air inlet bore (16). In addition, the revolver magazine (14) has an axial guide (17) for the pin (15).

Figure 7D:
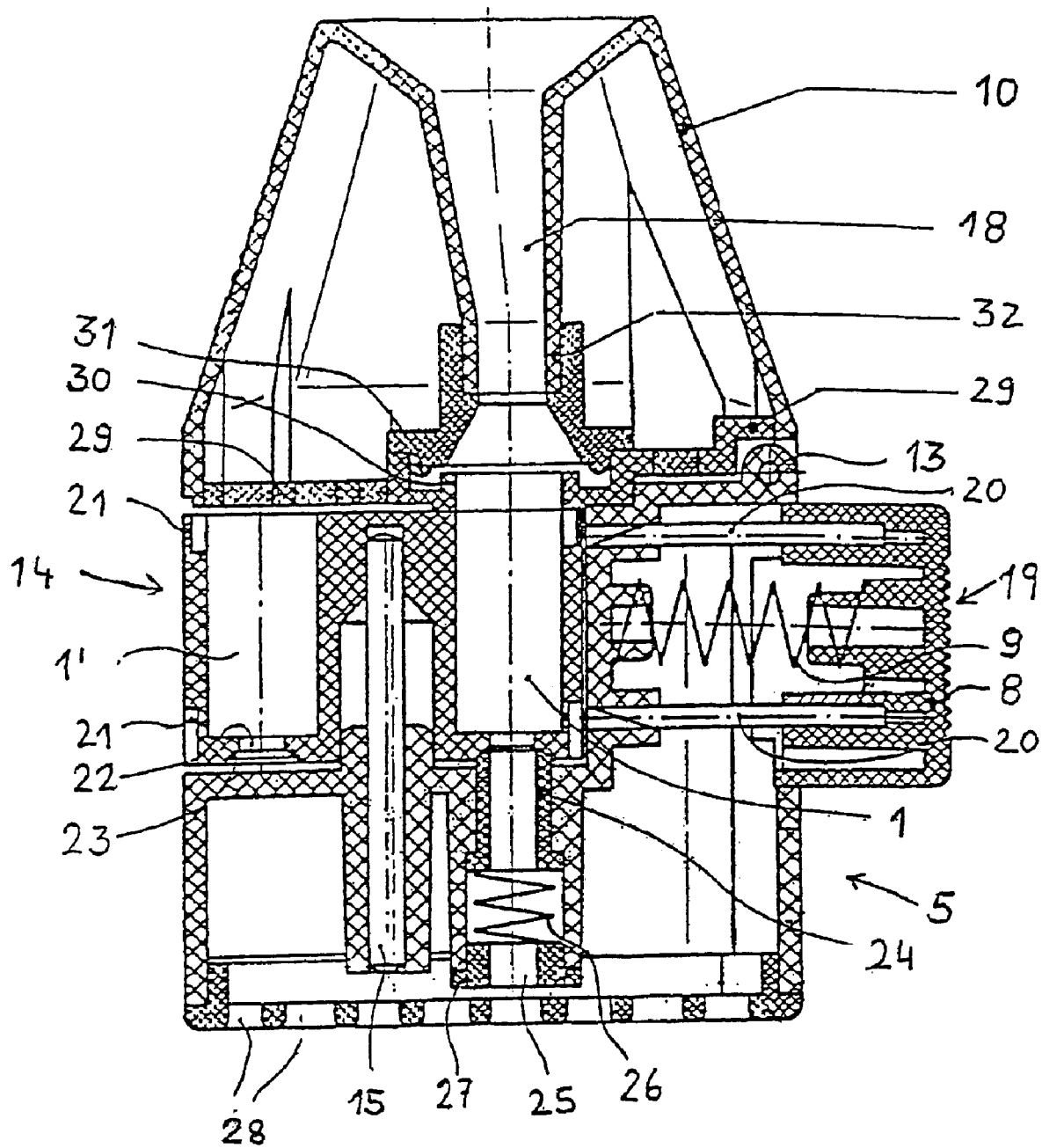

As may be seen from FIG. 7d, the inhaler has, adjacent to the chamber (1) mounted underneath the inhalation channel (18), the cutting device (19) which is operated by means of the button (8). This cutting device (19) has two spikes (20) which can be radially inserted into the upper and lower part, respectively, of said chamber (1), the outer wall of the revolver magazine having weakened or frangible regions (21) at suitable points to assist the insertion of the spikes (20). The spikes (20) serve to open the capsule located in the chamber (1) close to the upper and lower ends thereof. The revolver magazine (14) also has, underneath the bore (22), conical recesses (23) in which a locking bolt (24) can engage as soon as the corresponding chamber (1) is coaxial with the air inlet or inhalation channel (18) of the inhaler housing. The locking bolt is also conically formed at its end engaging in the recess (23). At the opposite end it is acted upon by a spring (26) which bears on a stopper (27) releasably fixed in the inhaler housing. This stopper, like the locking bolt, has a central through-bore which acts as an air inlet (25).

In order to prepare the inhaler, with the revolver magazine (14) in place, this magazine is rotated so that one of the chambers (1) is brought into a position in which the bore (22) in the base or the conical recess (23) is aligned coaxially with the air inlet opening (25). The positioning of the chamber (1) is made easier by the engagement of the locking bolt (24) in the recess (23). After the bolt has engaged, the air inlet opening (25) and the base opening (22) in the chamber (1) are in alignment. The cap of the capsule is positioned on the base opening (22) and closes it off. By actuation of the button (8) counter to the force of a spring (9) the cutting edges (20) are moved radially towards the chamber (1), first piercing the weakened regions (21) or entering corresponding openings in the side wall of the revolver magazine and finally opening the capsule at the top and bottom close to its ends. The hemispherical caps of the capsules should not be destroyed.

When air is then sucked through the mouthpiece (10), the air flowing into the chamber from the base openings (28) in the housing (5) and the air inlet (25) sets the capsule vibrating violently, produces turbulence in the powder in the capsule, mixes with it and is finally inhaled. The mouthpiece (10) is generally tubular in construction but may also be adapted to the shape of the mouth and flattened. Similarly, as an alternative to the embodiment shown, the mouthpiece may be arranged axially or at an angle to the axis of the chamber or laterally offset from the axis of the chamber.

At the base, the mouthpiece (10) may be provided with a plate-shaped insert (29) which is essentially solid. This plate-shaped insert (29) may also have perforations. Moreover, the start of the inhalation channel (18) may be covered with a screen which prevents the capsule or capsule fragments from being inhaled into the inhalation chamber (18) in the mouthpiece. Alternatively, projections may be provided on the wall at this point to hold the capsule back. The perforated plate is then preferably arranged in the center of the plate-shaped insert (29), advantageously clamped between a stop (30) on the plate (29) surrounding the air throughflow and the edge of a funnel-shaped connecting member (31), which is fitted on to the beginning (32) of the inhalation channel (19) in such a way that the edge of the funnel faces the plate-shaped insert (29) and engages therewith. The alternatively provided projections may also be arranged at this point.

The embodiment of the inhaler according to the invention as shown in FIG. 8 consists of the lower part (5) and the mouthpiece (10), which are fitted together. The lower part contains the air inlet channel (25) which is connected to the air inlet into the capsule chamber (1). The cutting device (19) is held in its normal position by a spring element (9). The mouthpiece (10) contains the capsule chamber (1). The inner surface structure thereof according to the invention is not shown, nor in FIGS. 6 and 7. Projections (33) which limit the play of the capsule project into the extension of the capsule chamber. A perforated plate (34) delimits the capsule chamber and prevents fragments of capsule from being inhaled, for example. The inhaler may be axially compressed counter to the pressure of a spring element (35), the upper edge of the lower part reaching the position (36). In this position the blades or points (20) of the cutting device (19) may penetrate through the opening (21) into the capsule chamber (1) and open the capsules secured therein.

In order to use the inhaler according to FIG. 8 the lower part (5) and mouthpiece (10) are pulled apart, the capsule is inserted and the two parts of the inhaler are fitted together. After being pressed back into position (36) counter to the spring element (35) the cutting device (19) is actuated and released again. Under the pressure of the spring element (35) the inhaler returns to the initial position shown in FIG. 8. The active substance formulation from the capsule (not shown) can now be inhaled by breathing in through the mouthpiece (10).

What is claimed is:

1. In a combination comprising a capsule and a medicinal powder inhaler device comprising,
   (a) a generally cylindrical capsule having an outer surface, a longitudinal axis and containing a pharmaceutically active inhalable medicament, and
   (b) a medicinal powder inhaler device comprising,
   (1) a capsule chamber for receiving the capsule, said capsule chamber having an inner surface, an inlet proximate a first end, for admitting air into the chamber and an outlet, proximate a second end, which communicates with a mouthpiece, the axis of the chamber being the line running between the first and second ends, by means of which mouthpiece a patient can draw by inhalation a stream of air which flows from the inlet, through the capsule chamber, wherein it admixes with medicament which has been released from a capsule that has been received by the chamber, thence through the outlet and finally from the mouthpiece from whence the patient may inhale the mixture of air and medicament, the inner surface of said capsule chamber and the outer surface of said capsule defining clearance along the longitudinal axis and clearance in a transverse direction sufficient to enable the capsule to vibrate longitudinally (in the direction of air flow) and also transversely (at right angles to the direction of flow) while remaining aligned substantially parallel to the chamber axis when air is caused to pass through the chamber in response to inhalation by the patient, the combination including raised elements on either the inner surface of said capsule chamber or the outer surface of said capsule, which raised elements align the axis of the capsule with the longitudinal axis of the capsule chamber and which extend into the clearance of the transverse direction to constrain the capsule such that, when it vibrates within the capsule chamber, movement back and forth along its longitudinal axis is permitted with essentially no transverse movement, and (2) means for piercing a capsule placed into the capsule chamber, to thereby release medicament from the capsule into the capsule chamber.

2. In a medicinal powder inhaler device comprising, (a) a capsule chamber having an inner surface, for receiving a generally cylindrical capsule having an outer surface, a longitudinal axis and containing a pharmaceutically active inhalable medicament, said capsule chamber having an inlet proximate a first end, for admitting air into the chamber and an outlet, proximate a second end, which communicates with a mouthpiece, the axis of the chamber being the line running between the first and second ends, by means of which mouthpiece a patient can draw by inhalation a stream of air which flows from the inlet, through the capsule chamber, wherein it admixes with medicament which has been released from a capsule that has been received by the chamber, thence through the outlet and finally from the mouthpiece from whence the patient may inhale the mixture of air and medicament, the inner surface of said capsule chamber and the outer surface of said capsule defining clearance along the longitudinal axis and clearance in a transverse direction sufficient to enable the capsule to vibrate longitudinally (in the direction of air flow) and also transversely (at right angles to the direction of flow) while remaining aligned substantially parallel to the chamber axis when air is caused to pass through the chamber in response to inhalation by the patient, the combination including raised elements on the inner surface of said capsule chamber, which raised elements align the axis of the capsule with the longitudinal axis of the capsule chamber and which extend into the clearance of the transverse direction to constrain the capsule such that, when it vibrates within the capsule chamber, movement back and forth along its longitudinal axis is permitted with essentially no transverse movement, and (b) means for piercing a capsule placed into the capsule chamber, to thereby release medicament from the capsule into the capsule chamber.

* * * * *